United States Patent [19]
Zalay et al.

[11] 4,137,227
[45] Jan. 30, 1979

[54] 1-ALKYL-1,4-DIHYDRO-4-OXO-7-TRIAZE-NYL-3-QUINOLINECARBOXYLIC ACIDS

[75] Inventors: Andrew W. Zalay, Albany; George Y. Lesher, Schodack, both of N.Y.

[73] Assignee: Sterling Drug Inc., New York, N.Y.

[21] Appl. No.: 828,339

[22] Filed: Aug. 29, 1977

[51] Int. Cl.$^2$ ............................................. C07C 107/00
[52] U.S. Cl. ..................................... 260/140; 424/226
[58] Field of Search ........................... 260/140; 424/226

[56] References Cited

U.S. PATENT DOCUMENTS 3,119,808  1/1964  Buckley et al. ...................... 260/155

OTHER PUBLICATIONS

Adams et al., J. Chem. Soc., 1949, pp. 3181ff.

Primary Examiner—Charles F. Warren
Attorney, Agent, or Firm—Robert K. Bair; B. Woodrow Wyatt

[57] ABSTRACT

Compounds useful as antibacterial agents are 1-R-1,4-dihydro-4-oxo-7-(BN—N=N)-3-quinolinecarboxylic acids (I), wherein: (a) BN is dimethylamino where R is methyl, ethyl, n-propyl, n-butyl, n-pentyl or n-octyl; (b) BN is diethylamino where R is n-propyl; or, (c) BN is 4-methyl-1-piperazinyl where R is ethyl. These compounds are prepared by reacting lower-alkyl 7-amino-1-R-1,4-dihydro-4-oxo-3-quinolinecarboxylate (II) with a mineral acid and an alkali nitrite in aqueous medium to produce the corresponding diazonium salt of said 7-aminoquinoline, reacting said diazonium salt with an amine of the formula BNH in the presence of an acid-acceptor to produce lower-alkyl 1-R-1,4-dihydro-4-oxo-7-(BN—N=N)-3-quinolinecarboxylate and hydrolyzing said 3-quinolinecarboxylate to produce the corresponding 3-carboxylic acid (I). The intermediate lower-alkyl 7-amino-1-R-1,4-dihydro-4-oxo-3-quinolinecarboxylate (II) are prepared in several steps by conventional means starting with m-aniline.

6 Claims, No Drawings

1-ALKYL-1,4-DIHYDRO-4-OXO-7-TRIAZENYL-3-QUINOLINECARBOXYLIC ACIDS

BACKGROUND OF THE INVENTION

1. Field of the Invention

This invention relates to triazenyl derivatives of 1-alkyl-1,4-dihydro-4-oxo-3-quinolinecarboxylic acids as antibacterial agents and to a process for their preparation.

2. Description of the Prior Art

In a paper entitled "Coupling Reactions of Aminoquinolines with Benzenediazonium Chloride. A Study of Orientation in the Quinoline Ring", Renshaw et al. [J. Am. Chem. Soc. 61, 3322 (1939)] show that the reaction of benzenediazonium chloride with 7-aminoquinoline yields 7-amino-8-phenylazoquinoline, whereas the same coupling reaction with 2-aminoquinoline and 3-aminoquinoline result respectively in the formation of "2-benzenediazoaminoquinoline" and "3-benzenediazoaminoquinoline", respectively, "diazoamino" being the same as "triazeno" or, as used hereinbelow, triazenyl.

Adams et al. [J. Chem. Soc. 1949, pp. 3181ff] converted 3-aminoquinoline into its diazonium salt by reaction with hydrochloric acid and an aqueous solution of sodium nitrite and then reacted with diazonium salt with dimethylamine to produce 3,3-dimethyl-1-(3'-quinolinyl)triazene.

Rondestvedt and Davis reported [J. Org. Chem. 22, 200 (1957)] the preparation of over 50 1-aryl-3,3-dialkyltriazenes "by coupling a diazonium salt with a secondary (occasionally primary) amine in basic medium", most of the compounds being those where "aryl" was phenyl or substituted-phenyl and including one quinoline compound, namely, 3,3-dimethyl-1-(3'-quinolinyl)triazene, the same compound that had been reported earlier by Adams et al., supra. It is not clear from the article whether 3,3-dimethyl-1-(3'-quinolinyl)triazene was found to be active or inactive in the preliminary anti-cancer screen. The 3,3-dimethyl-1-(3'-quinolinyl)-triazene is characterized as follows: "Explodes during microanalysis"; "Crude product is very unstable"; "Must be filtered and washed throughly with ice water, then recrystallized while wet"; "it is allowed to dry while crude, it decomposes in a puff of smoke"; "The purified material darkens rapidly, but less dramatically, on storage".

Lin et al. [ABSTRACT OF PAPERS, 173rd ACS Meeting, New Orleans, La., Mar. 20-25, 1977, Paper No. 74, Division of Medicinal Chemistry] synthesized various 6(7 or 8)-halo-4-(3,3-dimethyl-1-triazeno)quinolines by diazotization of the appropriate 4-amino-6(7 or 8)quinoline in fluoboric acid at −5° C. followed by coupling with dimethylamine. This abstract reported "Preliminary results indicate that 6-chloro, 7-chloro, and 8-chloro-4-(3,3-dimethyl-1-triazeno)quinolines are active (as potential anti-tumor agents), prolonging the life-span of mice bearing i.p. implanted P-388 tumor from 10 days for control animals to 16–18 days for treated mice at an i.p. dosage of 30 mg/kg". The 6-iodo, 6-bromo, 7-bromo, and 8-bromo analogs were reported as inactive against this tumor up to 40 mg/kg and the 6-bromo, 8-bromo and 8-chloro derivatives were reported to be active against mouse L-1210 leukemia, "increasing the life-span by 50%, 65% and 65% respectively at 30 to 40 mg/kg dosage".

SUMMARY OF THE INVENTION

The invention in its composition aspect relates to certain 1-alkyl-1,4-dihydro-4-oxo-7-(BN—N=N)-3-quinolinecarboxylic acids (I) which are useful as antibacterial agents.

The invention in its process aspect comprises reacting lower-alkyl 7-amino-1-(lower-alkyl)-1,4-dihydro-4-oxo-3-quinolinecarboxylate (II) with a mineral acid and an alkali nitrite in aqueous medium to produce the corresponding diazonium salt of said 7-aminoquinoline, reacting said diazonium salt with an amine of the formula BNH in the presence of an acid-acceptor to produce lower-alkyl 1-R-1,4-dihydro-4-oxo-7-(BN—N=N)-3-quinolinecarboxylate and hydrolyzing said 3-quinolinecarboxylate to produce the corresponding 3-quinolinecarboxylic acid (I).

DETAILED DESCRIPTION INCLUSIVE OF PREFERRED EMBODIMENTS

The invention in its composition aspect resides in the compounds having the formula I

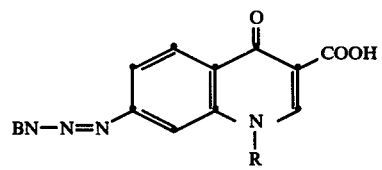

wherein a. BN is dimethylamino where R is methyl, ethyl, n-propyl, n-butyl, n-pentyl or n-octyl;
b. BN is diethylamino where R is n-propyl; or,
c. BN is 4-methyl-1-piperazinyl where R is ethyl.

The compounds of formula I possess the inherent applied use characteristics of having antibacterial activity, as determined by proven antibacterial evaluation procedures, and are useful as antibacterial agents.

The invention in its process aspect comprises reacting lower-alkyl 7-amino-1-R-1,4-dihydro-4-oxo-3-quinolinecarboxylate of the formula II

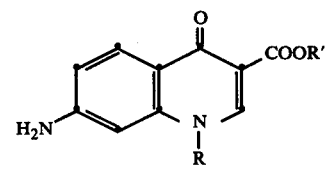

where R' is lower-alkyl and R is methyl, ethyl, n-propyl, n-butyl, n-amyl or n-octyl as defined in formula I hereinabove, with a mineral acid and an alkali nitrite in aqueous medium to produce the corresponding diazonium salt of said 7-aminoquinoline, reacting said diazonium salt with an amine of the formula BNH in the presence of an acid-acceptor to produce lower-alkyl 1-R-1,4-dihydro-4-oxo-7-(BN–N=N)-3-quinolinecarboxylate and hydrolyzing said 3-quinolinecarboxylate to produce the corresponding 3-quinolinecarboxylate acid of formula I.

The term "lower-alkyl" as used herein for the definition of R' of formula II, means alkyl radicals having from one to six carbon atoms which can be arranged as straight or branched chains, amoung which are, for purposes of illustration: methyl, ethyl, n-propyl, 2- butyl, isobutyl and n-hexyl, preferably ethyl and methyl.

The manner of making and using the instant invention will now be generally described so as to enable a person skilled in the art of pharmaceutical chemistry to make and use the same as follows:

The intermediate lower-alkyl 7-amino-1-R-1,4-dihydro-4-oxo-3-quinolinecarboxylates of formula II are prepared in several steps by convention procedures as follows: m-nitroaniline is reacted with diethyl ethoxymethylenemalonate to form diethyl m-nitroanilinomethylenemalonate which is cyclized by heating in an appropriate solvent such as Dowtherm® A (eutectic mixture of 26.5% diphenyl and 73.5% diphenyl ether) or mineral oil at about 250°–260° C. to produce lower-alkyl 1,4-dihydro-7-nitro-4-oxo-3-quinolinecarboxylate, which is then alkylated at the 1-position by reaction with an appropriate alkylating agent, e.g., methyl, ethyl or n-propyl halide, diethyl sulfate, triethyl phosphate, or the like, preferably in the presence of an inert solvent, e.g., dimethylformamide, and an appropriate acid-acceptor, e.g., anhydrous potassium carbonate, to produce lower-alkyl 1-R-1,4-dihydro-7-nitro-4-oxo-3-quinolinecarboxylate, catalytically hydrogenating the 7-nitro compound in the presence of an appropriate catalyst, e.g., palladium-on-charcoal, to produce the corresponding ethyl 7-amino-1-R-1,4-dihydro-4-oxo-3-quinolinecarboxylate (II).

The preparation of the diazonium salt of lower-alkyl 7-amino-1-R-1,4-dihydro-4-oxo-3-quinolinecarboxylate (II) is conveniently run by diazotizing the 7-amino group with nitrous acid in aqueous acidic medium, preferably using a mineral acid, e.g., hydrochloric acid, and alkali nitrite, e.g., sodium nitrite, at about $-5°$ C. to $0°$ C.

The reaction of the diazonium salt of the 7-aminoquinoline of formula II to produce the lower-alkyl 1-R-1,4-dihydro-7-(BN—N=N)-4-oxo-3-quinolinecarboxylate was carried out by reacting the diazonium salt at about 0° to 15° C. in the presence of an acid-acceptor, e.g., sodium carbonate, with the appropriate amine of the formula BNH where BN is defined hereinabove for the compounds of formula I.

The hydrolysis of the lower-alkyl 1-R-1,4-dihydro-7-(BN—N=N)-4-oxo-3-quinolinecarboxylate to produce the corresponding 1-R-1,4-dihydro-7-(BN—N=N)-4-oxo-3-quinolinecarboxylic acid can be carried out under aqueous acidic or alkaline reaction conditions. The reaction is conveniently run at room temperature, i.e., 20°–25° C., or warming up to 50°–80° C. if necessary to expedite the hydrolysis.

The antibacterial activity of the compounds of formula I was determined using a modification of the Autotiter® method described by Goss et al. [Applied Microbiology 16 (9), 1414-1416 (1968)] in which a 1,000 mcg./ml. solution of the test compound is prepared. To the first cup of the Autotray® is added 0.1 ml. of the test solution. Activation of the Autotiter initiates a sequence of operations by which 0.05 ml. of the test compound solution is withdrawn from the cup by a Microtiter® transfer loop and diluted in 0.05 ml. of sterile water. Following this operation, 0.05 ml. of inoculated double-strength semisynthetic medium (glucose) is added automatically to each cup. The overall operation results in final drug concentrations ranging from 500 to 0.06 mcg./ml. in twofold decrements. The Autotray is incubated for 18–20 hours at 37° C. at which time the trays are examined visually for growth as evidenced by turbidity, and the concentration of the last sample in the series showing no growth (or no turbidity) is recorded as the minimal inhibitory concentration (MIC) in mcg./ml. The compounds were thus tested as solutions and found active in the range of 7.8 to 125 mcg./ml. (MIC) against one or more of various gram positive and gram negative bacteria including *Staphylococcus aureus, Proteus mirabilis, Escherichia coli, Klebsiella pneumoniae* and *Streptococcus pyogenes.*

The actual determination of the numerical antibacterial data definitive for particular compounds of formula I is readily made by standard test procedures by technicians versed in antibacterial test procedures, without the need for any extensive experimentation.

The compounds of formula I can be formulated for use by preparing a dilute solution in an organic medium in which the compounds are soluble, for example, ethyl alcohol or in such solution containing a surfactant, and are applied to a surface to be disinfected by conventional methods such as spraying, swabbing, immersion, and the like. Alternatively, the compounds can be formulated as ointments or cream bases, for example alkylpolyether alcohols, cetyl alcohol, stearyl alcohol, and the like, or as jellies by incorporating them in conventional jelly bases such as glycerol and tragacanth.

The molecular structures of the compounds of the invention were assigned on the basis of evidence provided by their infrared, ultraviolet, nuclear magnetic resonance and mass spectra, by chromatographic mobilities, and confirmed by the correspondence between calculated and found values for their elementary analyses.

The following examples will further illustrate the invention without, however, limiting it thereto. All melting points are uncorrected.

A. LOWER-ALKYL 1,4-DIHYDRO-7-NITRO-4-OXO-3-QUINOLINECARBOXYLATES

A-1. Ethyl 1,4-Dihydro-7-nitro-4-oxo-3-quinolinecarboxylate — To a solution containing 207 g. of m-nitroaniline dissolved in 2750 ml. of Dowtherm® A (eutectic mixture of 26.5% diphenyl and 73.5% diphenyl ether) was added 342 g. of diethyl ethoxymethylenemalonate and the resulting reaction mixture was heated on a hot plate slowly over a 4 hour period to 230° C.; strong bubbling occurred around 150° C. The reaction mixture was stirred and heated to 250° C. (boiling) and then maintained at 252°–260° C. with stirring for 45 minutes; after about 30 minutes, yellow solid began to crystallize. The mixture was then allowed to cool with stirring and the resulting tan crystalline solid was collected and washed successively with ether and n-pentane and then dried in a vacuum oven at 80° C. to yield 133.6 g. of ethyl 1,4-dihydro-7-nitro-4-oxo-3-quinolinecarboxylate, m.p. >300° C.

B. LOWER-ALKYL 1-R-1,4-DIHYDRO-7-NITRO-4-OXO-3-QUINOLINECARBOXYLATES

B-1. Ethyl 1-ethyl-1,4-dihydro-7-nitro-4-oxo-3-quinolinecarboxylate — To a stirred mixture containing 277 g. of ethyl 1,4-dihydro-7-nitro-4-oxo-3-quinolinecarboxylate, 2000 ml. of dimethylformamide and 135.5 g. of anhydrous potassium carbonate heated on a steam bath was added 90 ml. of ethyl iodide. The reaction mixture was heated on a steam bath with stirring overnight (about 15 hours), allowed to cool and poured into 4000 ml. of water. The resulting yellow precipitate was collected, washed with water, air dried, dried in vacuo at 80° C. for 72 hours, stirred with dimethylformamide at room temperature, collected, rinsed with ethanol and dried in vacuo at 80° c. to yield 206 g. of ethyl 1-ethyl-1,4-dihydro-7-nitro-4-oxo-3-quinolinecarboxylate.

B-2. Ethyl 1,4-dihydro-1-methyl-7-nitro-4-oxo-3-quinolinecarboxylate — To a stirred suspension containing 64 g. of ethyl 1,4-dihydro-4-nitro-4-oxo-3-quinolinecarboxylate, 500 ml. of dimethylformamide and 36 g. of anhydrous potassium carbonate heated on a steam bath was added 42.5 g. of methyl iodide and the resulting mixture was heated on a steam bath with stirring for 20 hours, cooled and poured into 1200 ml. of water with stirring. The yellow precipitate was collected, washed well with fresh water, dried in a vacuum oven at 80° C., recrystallized from 250 ml. of dimethylformamide using decolorizing charcoal, washing with ether and drying in a vacuum oven at 80° C. to yield 45 g. of ethyl 1,4-dihydro-1-methyl-7-nitro-4-oxo-3-quinolinecarboxylate, m.p. 241°–245° C. B-3. Ethyl 1,4-dihydro-7-nitro-4-oxo-1-n-propyl-3-quinolinecarboxylate, m.p. 184°–185° C., 40.5 g. was prepared following the procedure described in Example B-2 using 64 g. of ethyl 1,4-dihydro-7-nitro-4-oxo-3-quinolinecarboxylate, 36 g. of anhydrous potassium carbonate, 500 ml. of dimethylformamide, 51 g. of n-propyl iodide, a heating period of 28 hours, and recrystallization first from dimethylformamide using decolorizing charcoal and then dissolving the once crystallized material in 500 ml. of methylene dichloride, filtering through diatomacious earth to remove a finely divided insoluble solid and then evaporating the filtrate in vacuo to yield said product.

It is contemplated that following the procedure described in Example B-2 using in place of methyl iodide a molar equivalent quantity of the appropriate alkyl halide, there will be obtained the following respective compounds of Examples B-4 through B-6.

B-4. Ethyl 1-n-butyl-1,4-dihydro-7-nitro-4-oxo-3-quinolinecarboxylate using n-butyl bromide.

B-5. Ethyl 1,4-dihydro-7-nitro-4-oxo-1-n-pentyl-3-quinolinecarboxylate using n-pentyl bromide.

B-6. Ethyl 1,4-dihydro-7-nitro-1-n-octyl-4-oxo-3-quinolinecarboxylate using n-octyl bromide.

C. LOWER-ALKYL 7-AMINO-1-R-1,4-DIHYDRO-4-OXO-4-QUINOLINECARBOXYLATES

C-1. Ethyl 7-amino-1-ethyl-1,4-dihydro-4-oxo-3-quinolinecarboxylate — A mixture containing 72.5 g. of ethyl 1-ethyl-1,4-dihydro-7-nitro-4-oxo-3-quinolinecarboxylate, 1200 ml. of dimethylformamide and 5 g. of 10% palladium-on-charcoal was hydrogenated at room temperature in a Parr shaker until the theoretical quantity of hydrogen was taken up (about 30 minutes). The reaction mixture was concentrated in vacuo; the remaining solid was combined with the same material obtained from an identical run and the combined solids were taken up in dilute hydrochloric acid. The palladium-on-charcoal catalyst was filtered off and the filtrate was basified with ammonium hydroxide. The resulting solid precipitate was collected, washed with water, recrystallized from dimethylformamide and dried at 80° C. to yield 105.8 g. of ethyl 7-amino-1-ethyl-1,4-dihydro-4-oxo-3-quinolinecarboxylate, m.p. 255°–257° C.

C-2. Ethyl 7-amino-1,4-dihydro-1-methyl-4-oxo-3-quinolinecarboxylate — A mixture containing 17.5 g. of ethyl 1,4-dihydro-1-methyl-7-nitro-4-oxo-3-quinolinecarboxylate, 2.0 g. of palladium-on-charcoal (10%) and 300 ml. of dimethylformamide was hydrogenated on a Parr shaker at 55° C. and an initial pressure of 51.8 p.s.i. After 70 minutes, the pressure had fallen to 35.8 p.s.i. and the uptake of hydrogen had ceased. The bottle was removed and heated on a steam bath for 15 minutes. Its contents were then filtered through diatomaceous earth and the filter pad washed with fresh dimethylformamide. The combined filtrates were allowed to cool overnight and then chilled in ice. The resulting crystalline precipitate was collected, washed with ether and dried in a vacuum oven at 80° C. to yield 10.7 g. of ethyl 7-amino-1,4-dihydro-1-methyl-4-oxo-3-quinolinecarboxylate, m.p. 276°–280° C.

C-3. Ethyl 7-amino-1,4-dihydro-4-oxo-1-n-propyl-3-quinolinecarboxylate, 7.2 g., m.p. 287°–288° C., was prepared following the procedure described in Example C-2 using 10.0 g. of ethyl 1,4-dihydro-7-nitro-4-oxo-1-n-propyl-3-quinolinecarboxylate, 300 ml. of dimethylformamide, 1.5 g. of 10% palladium-on-charcoal and initial pressure of 51.5 p.s.i. of hydrogen at 55° C. and a reaction period of 20 minutes.

It is contemplated that following the procedure described in Example C-2 using in place of ethyl 1,4-dihydro-1-methyl-7-nitro-4-oxo-3-quinolinecarboxylate a molar equivalent quantity of the appropriate corresponding ethyl 1-alkyl-1,4-dihydro-7-nitro-4-oxo-3-quinolinecarboxylate, there will be obtained the following respective compounds of Examples C-4 through C-6.

C-4. Ethyl 7-amino-1-n-butyl-1,4-dihydro-4-oxo-3-quinolinecarboxylate using the corresponding 7-nitro compound.

C-5. Ethyl 7-amino-1,4-dihydro-4-oxo-1-n-pentyl-4-oxo-3-quinolinecarboxylate using the corresponding 7-nitro compound.

C-6. Ethyl 7-amino-1,4-dihydro-1-n-octyl-4-oxo-3-quinolinecarboxylate using the corresponding 7-nitro compound.

D. LOWER-ALKYL 1-R-1,4-DIHYDRO-7-(BN—N=N)-4-OXO-3-QUINOLINECARBOXYLATES

D-1. Ethyl 1-ethyl-7-(3,3-dimethyl-1-triazenyl)-1,4-dihydro-4-oxo-3-quinolinecarboxylate — To a mixture containing 69 ml. of concentrated hydrochloric acid and 400 g. of ice was added in portions with stirring 52 g. of ethyl 7-amino-1-ethyl-1,4-dihydro-4-oxo-3-quinolinecarboxylate. To this stirred mixture was added dropwise (the stem of the dropping funnel reaching below the surface of the reaction mixture) a solution containing 14 g. of sodium nitrite in 45 ml. of water. The light brown clear reaction mixture was kept at −5° C. for 30 minutes and to its was added dropwise using a precooled dropping funnel first a solution of 100 g. of sodium carbonate in 250 ml. of water followed by 110 ml. of 40% aqueous dimethylamine solution, keeping the reaction mixture at about 0° to 15° C. using an outside methanol-ice bath. The buff colored crystalline product was collected, washed with water and dissolved in methylene dichloride. The methylene dichloride solution was washed with water, dried over anhydrous magnesium sulfate and treated with n-hexane to precipitate the product. There was thus obtained 53 g. of the product, ethyl 1-ethyl-7-(3,3-dimethyl-1- triazenyl)-1,4-dihydro-4-oxo-3-quinolinecarboxylate, m.p. 141°–142° C., after drying in vacuo at 80° C. for 18 hours. A second cup of 4.8 g. of the product, m.p. 141°–142° C., was obtained from the mother liquor.

D-2. Ethyl 1,4-dihydro-1-methyl-7-(3,3-dimethyl-1-triazenyl)-4-oxo-3-quinolinecarboxylate — To a stirred mixture containing 12.3 g. of ethyl 7-amino-1,4-dihydro-1-methyl-4-oxo-3-quinolinecarboxylate, 400 ml. of water and 17 ml. of concentrated hydrochloric acid, and kept below 0° C. using a methanol-ice bath, was added dropwise through a tube dipping below the surface of the reaction mixture a solution containing 3.5 g. of sodium nitrite dissolved in 15 ml. of water, the addition requiring about 6 minutes. The reaction mixture was stirred well and then removed from the cold bath. This mixture containing in solution the diazonium salt of the said 7-aminoquinoline was filtered to remove a small amount of yellow solid and the filtrate was added dropwise with stirring to a chilled mixture containing 25 g. of sodium carbonate, 100 ml. of water and 40 ml. of 40% aqueous dimethylamine, said mixture stirred and cooled in a methanol-ice bath; the addition required about 20 minutes. The methanol-ice bath was removed and the reaction mixture stirred for an additional 15 minutes. The white solid was collected, washed with a small amount of fresh water and was recrystallized from 250 ml. of acetonitrile using decolorizing charcoal and dried in a vacuum oven at 80° C. to yield 12.1 g. of ethyl 1,4-dihydro-1-methyl-7-(3,3-dimethyl-1-triazenyl)-4-oxo-3-quinolinecarboxylate, m.p. 194.5°–196° C.

D-3. Ethyl 1,4-dihydro-7-(3,3-dimethyl-1-triazenyl)-4-oxo-1-n-propyl-3-quinolinecarboxylate, 10.8 g., m.p. 155°–157° C., was prepared following the procedure described in Example D-2; using 13.7 g. of ethyl 7-amino-1,4-dihydro-4-oxo-1-n-propyl-3-quinolinecarboxylate, 3.0 g. of sodium nitrite, 17 ml. of concentrated hydrochloric acid, 200 ml. of water first to prepare the diazonium salt of said 7-aminoquinoline; reacting the diazonium salt with 40 ml. of aqueous dimethylamine and 50 g. of sodium carbonate in 200 ml. of water; and, purifying the product by dissolving it in methylene dichloride, drying the solution over anhydrous magnesium sulfate, stirring the dry solution with decolorizing charcoal and filtering, and recrystallizing the product from 50 ml. of acetonitrile and drying it in a vacuum oven at 80° C.

D-4. Ethyl 7-(3,3-diethyl-1-triazenyl)-1,4-dihydro-4-oxo-1-n-propyl-3-quinolinecarboxylate, 19.1 g., m.p. 100°–102° C., was prepared following the procedure described in Example D-2: first using 14.8 g. of ethyl 7-amino-1,4-dihydro-4-oxo-1-n-propyl-3-quinolinecarboxylate, 3.8 g. of sodium nitrite, 37 ml. of concentrated hydrochloric acid and 400 ml. of water to prepare the diazonium salt of the 7-aminoquinoline; reacting diazonium salt with 30 ml. of diethylamine and 50 g. of sodium carbonate in 200 ml. of water; and, purifying the product by taking it up in 200 ml. of methylene dichloride, washing the methylene dichloride solution twice with water, drying it over anhydrous magnesium sulfate, evaporating off the methylene dichloride and triturating the resulting viscous syrup in ether and then drying the resulting solid crystalline product.

D-5. Ethyl 1-ethyl-1,4-dihydro-7-[(4-methyl-1-piperazinyl)azo]-4-oxo-3-quinolinecarboxylate, 11.2 L g., m.p. 162°–163° C., was prepared following the procedure described in Example D-2: first using 13.0 g. of ethyl 7-amino-1-ethyl-1,4-dihydro-4-oxo-3-quinolinecarboxylate, 3.5 g. of sodium nitrite, 17 ml. of hydrochloric acid and 150 ml. of water to prepare the diazonium salt of said 7-aminoquinoline; reacting said diazonium salt with 15 ml. of N-methylpiperazine and 25 g. of sodium carbonate in 100 ml. of water; and, purifying the product by taking it up in 250 ml. of methylene dichloride, washing the methylene dichloride solution twice with water, drying it over anhydrous magnesium sulfate, filtering and diluting the cooled filtrate with 500 ml. of n-hexane, collecting and drying the resulting precipitate, recrystallizing it from 90 ml. of acetonitrile using decolorizing charcoal and drying the product in a vacuum oven at 80° C.

It is contemplated that following the procedure described in Example D-2 using in place of ethyl 7-amino-1,4-dihydro-1-methyl-4-oxo-3-quinolinecarboxylate a molar equivalent quantity of the appropriate ethyl 1-alkyl-7-amino-1,4-dihydro-4-oxo-3-quinolinecarboxylate, there will be obtained the following respective compounds of Examples D-6 through D-8.

D-6. Ethyl 1-n-butyl-1,4-dihydro-7-(3,3-dimethyl-1-triazenyl)-4-oxo-3-quinolinecarboxylate using ethyl 7-amino-1-n-butyl-1,4-dihydro-4-oxo-3-quinolinecarboxylate.

D-7. Ethyl 1,4-dihydro-7-(3,3-dimethyl-1-triazenyl)-1-n-octyl-4-oxo-3-quinolinecarboxylate using ethyl 7-amino-1,4-dihydro-1-n-octyl-4-oxo-3-quinolinecarboxylate.

D-8. Ethyl 1,4-dihydro-7-(3,3-dimethyl-1-triazenyl)-4-oxo-1-n-pentyl-3-quinolinecarboxylate using ethyl 7-amino-1,4-dihydro-4-oxo-1-n-pentyl-3-quinolinecarboxylate.

E.
1-R-1,4-DIHYDRO-4-OXO-7-(BN—N=N)-3-QUINOLINECARBOXYLIC ACIDS

E-1.    1-Ethyl-1,4-dihydro-7-(3,3-dimethyl-1-triazenyl)-4-oxo-3-quinolinecarboxylic Acid — To a solution containing 23.2 g. of ethyl 1-ethyl-1,4-dihydro-7-(3,3-dimethyl-1-triazenyl)-4-oxo-3-quinolinecarboxylate dissolved in 500 ml. of methanol was added 6.3 ml. of 35% aqueous sodium hydroxide solution. The reaction mixture was allowed to stand at room temperature for 4 hours and then concentrated in vacuo at 30° C. to yield 26 g. of a brownish transparent solid. The solid was dissolved in 300 ml. of distilled water; some insoluble material (about 1.5 g.) was filtered off; and, the filtrate was cooled to 2° C., acidified with 3 ml. of acetic acid in 20 ml. of water. The resulting crystalline precipitate was collected, washed with water, recrystallized from chloroform and dried overnight in vacuo at 80° C. to yield 8.5 g. of 1-ethyl-1,4-dihydro-7-(3,3-dimethyl-1-triazenyl)-4-oxo-3-quinolinecarboxylic acid, m.p. 261°–263° C.

E-2.    1,4-Dihydro-1-methyl-7-(3,3-dimethyl-1-triazenyl)-4-oxo-3-quinolinecarboxylic Acid — To a suspension containing 12.1 g. of ethyl 1,4-dihydro-1-methyl-7-(3,3-dimethyl-1-triazenyl)-4-oxo-3-quinolinecarboxylate in 500 ml. of methanol was added 3.4 ml. of 35% aqueous sodium hydroxide solution and the resulting light red solution was allowed to stand at room temperature for 18 hours. The reaction mixture was evaporated using a rotary evaporater keeping the water bath temperature at 30°–40° C., whereupon there was obtained about 31 g. of solid material which was shaken well with 500 ml. of water. To this mixture was added slowly 2.5 g. of acetic acid in 15 ml. of water and the precipitated solid was collected, washed with fresh water, recrystallized from 100 ml. of dimethylformamide using decolorizing charcoal, washed with ether and dried in a vacuum oven at 80° C. to yield 7.7 g. of product. The product was taken up in 800 ml. of water containing 0.035 mole of potassium hydroxide at room temperature, filtered and the filtrate neutralized with dilute acetic acid whereupon copious cream colored solid formed. The mixture was stirred well and the solid was collected, washed with water and recrystallized from 150 ml. of dimethylformamide using decolorizing charcoal, washing the recrystallized product with ether and drying it in a vacuum oven at 80° C. to produce 4.5 g. of 1,4-dihydro-1-methyl-7-(3,3-dimethyl-1-triazenyl)-4-oxo-3-quinolinecarboxylic acid, m.p. 278°-281° C. with decomposition.

E-3. 1,4-Dihydro-7-(3,3-dimethyl-1-triazenyl)-4-oxo-1-n-propyl-3-quinolinecarboxylic Acid — To a stirred mixture containing 10.8 g. of ethyl 1,4-dihydro-7-(3,3-dimethyl-1-triazenyl)-4-oxo-1-n-propyl-3-quinolinecarboxylate in 150 ml. of water at room temperature was added 2.8 ml. of 35% aqueous sodium hydroxide solution and the resulting mixture was allowed to stand for 18 hours at room temperature. The solution was then evaporated on a rotary evaporator at room pressure, keeping the temperature of the water bath at about 30°-40° C. The residual material was taken up in 100 ml. of water and filtered. The filtrate was acidified with stirring using 2.0 g. of acetic acid in 20 ml. of water whereupon a very pale yellow solid separated; the volume had to be increased to 400 ml. by addition of water in order to facilitate the stirring. The solid was collected, washed with fresh water, and dried in a vacuum oven at 80° C., recrystallized from 800 ml. of 95% ethanol and dried in a vacuum oven at 80° C. to produce 8.8 g. of 1,4-dihydro-7-(3,3-dimethyl-1-triazenyl)-4-oxo-1-n-propyl-3-quinolinecarboxylic acid, m.p. 221°-222° C.

E-4. 7-(3,3Diethyl-1-triazenyl)-1,4-dihydro-4-oxo-1-n-propyl-3-quinolinecarboxylic Acid, m.p. 187°-188° C., 10.9 g., was obtained following the procedure described in Example E-3 using 19.1 g. of ethyl 7-(3,3-diethyl-1-triazenyl)-1,4-dihydro-4-oxo-1-n-propyl-3-quinolinecarboxylate, 200 ml. of methanol, 4.6 ml. of 35% aqueous sodium hydroxide solution and recrystallization from absolute ethanol using decolorizing charcoal.

E-5. 1-Ethyl-1,4-dihydro-7-[(4-methyl-1-piperazinyl)azo]-4-oxo-3-quinolinecarboxylic Acid, m.p. 236°-238° C. with decomposition, 7.3 g., was prepared following the procedure described in Example E-3 using 11.7 g. of ethyl 1-ethyl-1,4-dihydro-7-[(4-methyl-1-piperazinyl)azo]-4-oxo-3-quinolinecarboxylate, 2.6 ml. of 35% aqueous sodium hydroxide solution, 150 ml. of methanol and recrystallization from 600 ml. of acetonitrile using decolorizing charcoal.

When tested by the antibacterial in vitro Autotiter ® testing method described hereinabove, the compounds of Examples E-1 through E-5 were found to have the minimal inhibitory concentrations (MIC's) against the indicated bacteria in Table A.

Table A

| Bacteria | MIC (mcg/ml) | | | | |
|---|---|---|---|---|---|
| | E-1 | E-2 | E-3 | E-4 | E-5 |
| S. aureus (Smith) | 15.6 | 62.5 | >62.5 | 62.5 | 31.3 |
| E. coli (Vogel) | 7.8 | 125 | >62.5 | >500 | 15.6 |
| Kleb. pneumoniae | 500 | >125 | >125 | >500 | 62.5 |
| Prot. mirabilis | (a) | >125 | >125 | >500 | 125 |
| E. coli (1100/B22) | (a) | >250 | >62.5 | >500 | 15.6 |
| Strep. pyogens | 125 | 62.5 | 31.3 | 62.5 | 125 |

(a) Not tested

It is contemplated that following the procedure described in Example E-3 using in place of ethyl 1,4-dihydro-7-(3,3-dimethyl-1-triazenyl)-4-oxo-1-n-propyl-3-quinolinecarboxylate a molar equivalent quantity of the appropriate ethyl 1-alkyl-1,4-dihydro-7-(3,3-dimethyl-1-triazenyl)-4-oxo-3-quinolinecarboxylate, there will be obtained the following respective compounds of Examples E-6 through E-8.

E-6. 1-n-Butyl-1,4-dihydro-7-(3,3-dimethyl-1-triazenyl)-4-oxo-3-quinolinecarboxylic acid using the corresponding ethyl ester.

E-7. 1,4-Dihydro-7-(3,3-dimethyl-1-triazenyl)1-n-octyl-4-oxo-3-quinolinecarboxylic acid using the corresponding ethyl ester.

E-8. 1,4-Dihydro-7-(3,3-dimethyl-1-triazenyl)-4-oxo-1-n-pentyl-3-quinolinecarboxylic acid using the corresponding ethyl ester.

We claim:

1. A compound having the formula

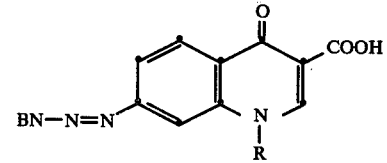

wherein
a. BN is dimethylamino where R is methyl, ethyl, n-propyl, n-butyl, n-pentyl or n-octyl;
b. BN is diethylamino where R is n-propyl; or
c. BN is 4-methyl-1-piperazinyl where R is ethyl.

2. 7-(3,3-Dimethyl-1-triazenyl)-1,4-dihydro-1-methyl-4-oxo-3-quinolinecarboxylic acid according to claim 1.

3. 1-Ethyl-7-(3,3-dimethyl-1-triazenyl)-1,4-dihydro-4-oxo-3-quinolinecarboxylic acid according to claim 1.

4. 1,4-dihydro-7-(3,3-dimethyl-1-triazenyl)-4-oxo-1n-propyl-3-quinolinecarboxylic acid according to claim 1.

5. 7-(3,3-Diethyl-1-triazenyl)-1,4-dihydro-4-oxo-1-n-propyl-3-quinolinecarboxylic acid according to claim 1.

6. 1-Ethyl-1,4-dihydro-7-[(4-methyl-1-piperazinyl)azo]-4-oxo-3-quinolinecarboxylic acid according to claim 1.

* * * * *

UNITED STATES PATENT AND TRADEMARK OFFICE
CERTIFICATE OF CORRECTION

PATENT NO. : 4,137,227
DATED : January 30, 1979
INVENTOR(S) : Andrew W. Zalay and George Y. Lesher It is certified that error appears in the above-identified patent and that said Letters Patent are hereby corrected as shown below:

Column 1, line 27, "reacted with diazonium" should read -- reacted the diazonium --.

Column 5, line 22, a new paragraph should start beginning with "B-3. Ethyl".

Column 7, line 64-65, "11.2 L g.," should read -- 11.2 g., --.

Column 9, line 37, "7-(3,3Diethyl-1-triazenyl)-" should read -- 7-(3,3-Diethyl-1-triazenyl)- --.

Column 10, line 51, "-ln-propyl-" should read -- -1-n-propyl- --.

Signed and Sealed this

Twelfth Day of August 1980

[SEAL]

Attest:

SIDNEY A. DIAMOND

Attesting Officer

Commissioner of Patents and Trademarks